US00PP29110P2

(12) United States Plant Patent
Blom

(10) Patent No.: US PP29,110 P2
(45) Date of Patent: Mar. 13, 2018

(54) ***ASTER* PLANT NAMED 'X WHITE'**

(50) Latin Name: *Aster alpinus*
Varietal Denomination: X White

(71) Applicant: Arie Blom, Vleuten (NL)

(72) Inventor: Arie Blom, Vleuten (NL)

( * ) Notice: Subject to any disclaimer, the term of this patent is extended or adjusted under 35 U.S.C. 154(b) by 15 days.

(21) Appl. No.: 14/999,175

(22) Filed: Apr. 7, 2016

(51) Int. Cl.
*A01H 5/02* (2006.01)

(52) U.S. Cl.
USPC ..... Plt./355

(58) Field of Classification Search
USPC ..... Plt./355

CPC . A01H 5/025; A01H 5/02; A01H 5/00; A01H 5/0227

See application file for complete search history.

(56) References Cited

PUBLICATIONS

CNB New Plants catalogue retrievec on Jun. 21, 2017, retrieved from the Internet at <http://www.cnb.nl/EN/Pages/Product-Catalog.aspx?ProductId=231> one page.*

* cited by examiner

*Primary Examiner* — June Hwu
(74) *Attorney, Agent, or Firm* — Penny J. Aguirre

(57) ABSTRACT

A new cultivar of *Aster* named 'X White' that is characterized by its inflorescences that are fully double and white in color and its compact plant height.

2 Drawing Sheets

Botanical classification: *Aster alpinus.*
Variety denomination: 'X White'.

CROSS REFERENCE TO A RELATED APPLICATION

This application is co-pending with U.S. Plant Patent Applications filed for plants derived from the same breeding program that are entitled *Aster* Plant Named 'X Blue' (U. S. Plant patent application Ser. No. 14/999,174) and *Aster* Plant Named 'X Pink' (U. S. Plant patent application Ser. No. 14/999,173).

BACKGROUND OF THE INVENTION

The present invention relates to a new and distinct cultivar of *Aster alpinus*, botanically known as *Aster* 'X White', and will be referred to hereafter by its cultivar name, 'X White'. 'X White' is a new herbaceous perennial suitable for use as a landscape and container plant.

The new invention arose from an ongoing controlled breeding program by the Inventor in Vleuten, The Netherlands. The objectives of the breeding program are to develop new cultivars of *Aster alpinus* with compact habits and double flowers.

'X White' derived from open pollination in May of 2010 of an unnamed and unpatented plant of *Aster alpinus* from the Inventor's breeding program, reference no. 1001-03 (not patented), as the female parent. 'X White' was selected in June of 2012 as a single unique plant amongst the resulting seedlings.

Asexual reproduction of the new cultivar was first accomplished by cuttings in Noordwijk, The Netherlands in August of 2012 under the direction of the Inventor. Asexual propagation by tissue culture using meristem tissue and stem cuttings has determined that the characteristics of this cultivar are stable and are reproduced true to type in successive generations.

SUMMARY OF THE INVENTION

The following traits have been repeatedly observed and represent the characteristics of the new cultivar. These attributes in combination distinguish 'X White' as a new and unique cultivar of *Aster.*

1. 'X White' exhibits inflorescences that are fully double and white in color.
2. 'X White' exhibits a compact plant habit.

The female parent of 'X White', reference no. 1001-03, differs from 'X White' in having a less vigorous growth habit. 'X White' can also be compared to *Aster* cultivars 'X Blue' and 'X Pink'. Both 'X Blue' and 'X Pink' are similar to 'X White' in having double inflorescences. 'X Blue' differs from 'X White' in having inflorescences that are purple-blue in color and in having disc flowers that are slightly shorter in length. 'X Pink' is similar to 'X White' in having double inflorescences. 'X Pink' differs from 'X White' in having inflorescences that are pink in color.

BRIEF DESCRIPTION OF THE DRAWINGS

The accompanying colored photographs illustrate the overall appearance and distinct characteristics of the new cultivar. The photographs were taken of a plant about six months in age as field grown Noordwijk, The Netherlands and placed in a container for the photographs.

Figure 1:
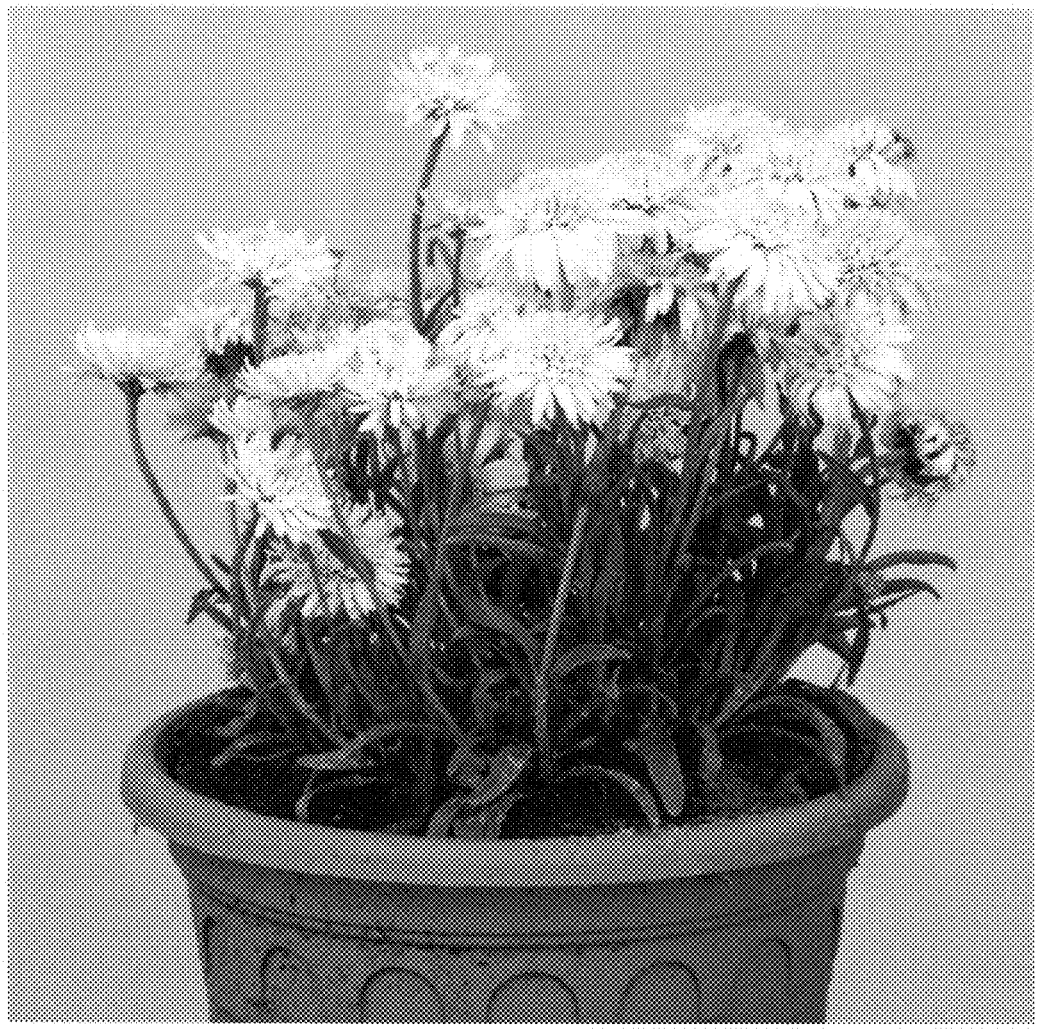
FIG. 1 provides a side view of the plant habit of 'X White' in bloom.
Figure 2:
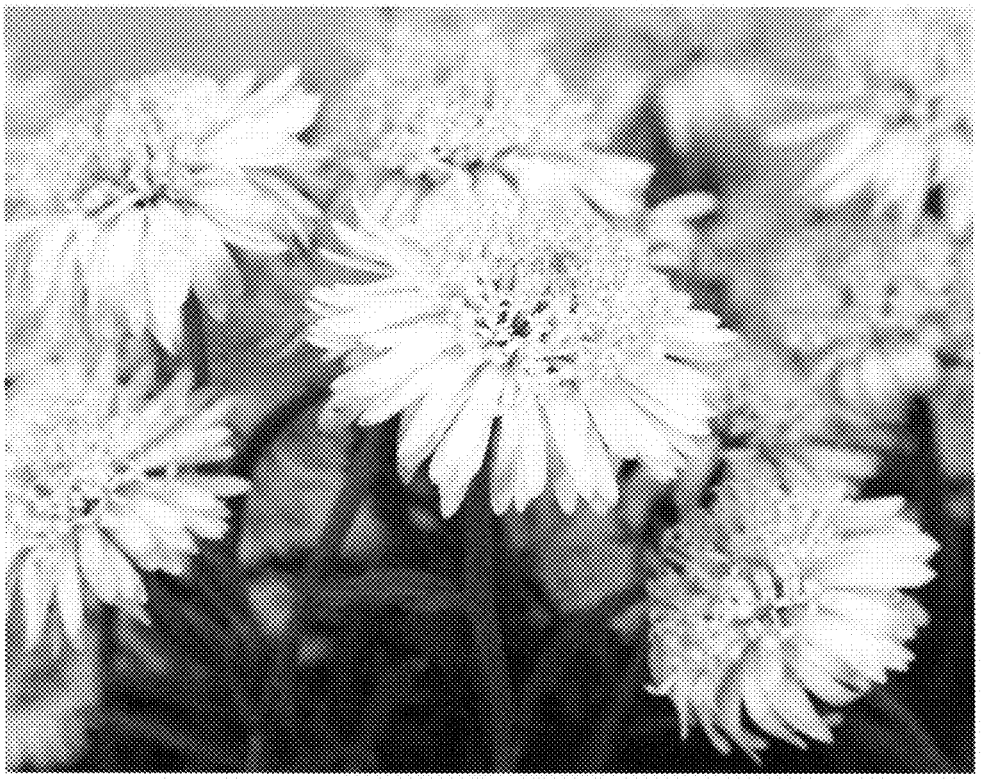
FIG. 2 provides a view of the inflorescences of 'X White'.
Figure 3:
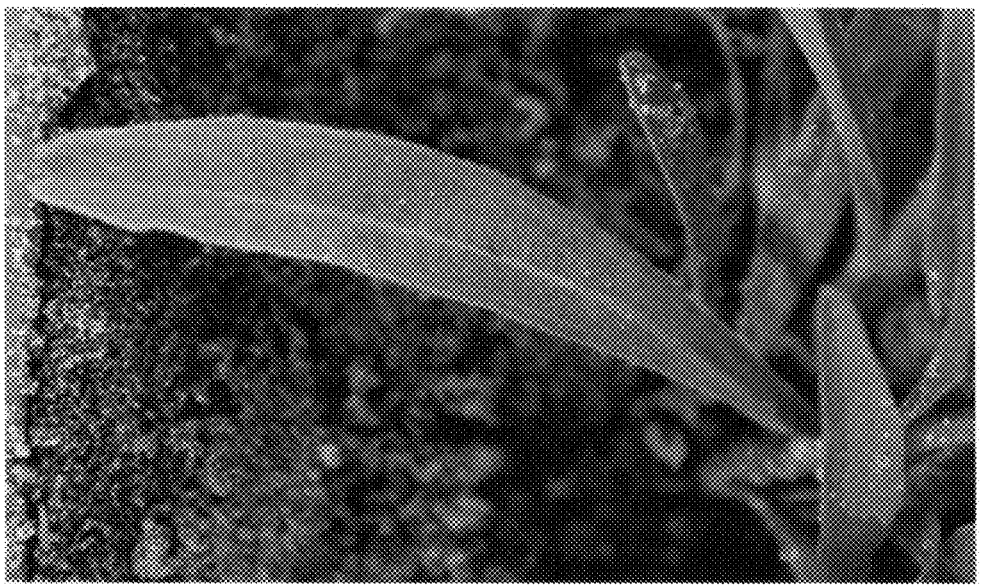
FIG. 3 provides a view of the foliage of 'X White'.

The colors in the photographs are as close as possible with digital photography techniques available, the color values cited in the detailed botanical description accurately describe the colors of the new *Aster*.

DETAILED BOTANICAL DESCRIPTION

The following is a description of six month-old plants of the new cultivar as field grown in Noordwijk, The Netherlands. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General description:

*Blooming season.*—From May to June in The Netherlands.

*Plant type.*—Herbaceous perennial.

*Plant habit.*—Compact, upright mound.

*Height and spread.*—Reaches a height of 25 cm and a spread of 30 cm.

*Hardiness.*—At least in U.S.D.A. Zone 4.

*Diseases resistance.*—No resistance or susceptibility to diseases has been observed.

*Root description.*—Fibrous and 158D in color.

*Root development.*—A rooted tissue culture plantlet will fully root in a 4-cm liner in 6 to 8 weeks.

*Propagation.*—Tissue culture from meristem tissue and stem cuttings.

*Growth rate.*—Moderate.

Stem description:

*Stem shape.*—Round.

*Stem color.*—144A.

*Stem surface.*—Moderately glossy and moderately covered with soft pubescence; an average of 0.3 mm and 157D in color.

*Stem size.*—An average of 18.9 cm in length (including peduncle) and 2.5 mm in diameter.

*Stem strength.*—Strong.

*Stem aspect.*—Slightly angled, held at an average angle of 60° to soil level, varying between 30° and 90°.

*Branching habit.*—Average of 48 branches, main stems grow from base, branched into lateral stems.

*Branch internode length.*—2.4 cm in length.

Foliage description:

*Leaf division.*—Simple.

*Leaf shape.*—Narrow oblanceolate.

*Leaf base.*—Long and narrow cuneate.

*Leaf apex.*—Obtuse.

*Leaf margin.*—Entire and moderately covered with very short strigose hairs, average of 0.3 mm in length and NN155D in color.

*Leaf venation.*—Pinnate, upper and lower surface 144B.

*Leaf attachment.*—Sessile.

*Leaf arrangement.*—Alternate.

*Leaf number.*—Average of 8 per stem.

*Leaf surface.*—Upper surface is moderately glossy, lower surface is slightly glossy, both surfaces are slightly rough to the touch and covered with very short hairs average of 0.3 mm in length and to small to measure with RHS-CC.

*Leaf color.*—Young upper surface; 137D, young and mature lower surface; between 137C and 147B, mature upper surface; 137C.

*Leaf size (fully expanded).*—Average of 5 cm in length and 9 mm in width.

Flower description:

*Inflorescence type.*—Composite, 1 per lateral stem.

*Lastingness of individual capitulum.*—Temperature dependent, typically last 4 to 5 weeks.

*Rate of opening.*—Disc florets at the margin open first, followed by the disc florets in the center of each inflorescence.

*Fragrance.*—Faint.

*Quantity of capitulum.*—An average of 48 per plant.

*Capitulum buds.*—Average of 1.6 cm in length and 1.2 cm in diameter, ovate in shape, color; 143C, base 144D, top NN155D, surface is glabrous with base pubescent.

*Capitulum size.*—About 1.3 cm in diameter and 8 mm in depth, diameter of disk about 5 mm.

*Peduncle.*—Terminal peduncle held straight on top of stem, moderate strength, 4 cm in length and 3 mm in width, 144A in color, surface moderately glossy and moderately covered with soft pubescence; an average of 0.3 mm and 157D in color.

*Involucral bracts.*—Average of 45 per inflorescence, placed spirally in three rows, lanceolate, entire margins, acute apex, cuneate base, 1 cm in length and 0.2 mm in width, surface color; upper surface 144C, lower surface 144B, upper and lower surface densely covered with very short pubescence, upper surface is 0.23 mm in length and 157D in color, lower surface is 0.2 mm in length and 157D in color.

Ray florets (carpellate):

*Number.*—Average of 84 per inflorescence.

*Shape.*—Narrow oblanceolate.

*Arrangement.*—Rotate, placed around disc in 2 rows.

*Aspect.*—Slightly upright at the base, in an average angle of 40°, tip or ray floret pointed downward in an average angle of −90°.

*Size.*—Average of 2.2 cm in length and 3 mm in width.

*Apex.*—Acute to praemorse.

*Base.*—Cuneate.

*Margins.*—Entire.

*Surface.*—Upper surface is glabrous, very slightly glossy and velvety, lower surface is glabrous and moderately glossy, base is covered with soft hairs an average of 25 hairs, 5 mm in length and 150D in color.

*Color.*—When opening and fully open upper and lower surface; NN155D.

Disk florets (perfect):

*Quantity.*—Average of 140 per inflorescence.

*Shape.*—Tubular with an average of 4 free tips, occasionally 5 free tips, spirally placed on disc, lower 85% fused into a tube, free lobes with acute tips.

*Surface.*—Both surfaces glabrous and moderately glossy, base is covered with soft hairs an average of 25 hairs, 5 mm in length and 150D in color.

*Margin.*—Entire.

*Size.*—About 1.4 cm in length and 5 mm in width.

*Color.*—When opening and fully open upper surface; base and mid-section NN155B, free tips NN155A, outer tip 154D, when opening and fully open lower surface; base and mid-section NN155B, free tips NN155A.

Reproductive organs:

*Presence.*—Disk florets are perfect, ray florets are carpellate.

*Gynoecium.*—Pistil; 1 per disk and ray floret, style; is 3 mm in length and 150D in color, ovary; is 145C.

*Androecium.*—5 stamens per disk floret, anther; linear in shape, 177C in color and 2 mm in length, filament; 9 mm in length and 145D in color, pollen; quantity is moderate and 13A in color.

*Fruit and seed.*—None produced to date.

It is claimed:

1. A new and distinct cultivar of *Aster* plant named 'X White' as described and illustrated herein.

* * * * *